United States Patent [19]

Nieto et al.

[11] Patent Number: 4,976,724

[45] Date of Patent: Dec. 11, 1990

[54] LANCET EJECTOR MECHANISM

[75] Inventors: Robert L. Nieto, Pleasanton; Chris W. Rasmussen, Felton, both of Calif.

[73] Assignee: LifeScan, Inc., Mountain View, Calif.

[21] Appl. No.: 398,582

[22] Filed: Aug. 25, 1989

[51] Int. Cl.⁵ .............................................. A61B 17/32
[52] U.S. Cl. .................................................... 606/182
[58] Field of Search ........ 606/181, 182, 167, 183–189; 604/46, 47, 48; 128/760; 30/260, 349, 336, 346 S, 40.2

[56] References Cited

U.S. PATENT DOCUMENTS

| 4,379,456 | 4/1983 | Cornell et al. | 128/314 |
| 4,503,856 | 3/1985 | Cornell et al. | 606/182 |
| 4,517,978 | 5/1985 | Levin et al. | 128/314 |
| 4,658,821 | 4/1987 | Chiodo et al. | 606/182 |

*Primary Examiner*—Max Hindenburg
*Assistant Examiner*—Robin R. Longo
*Attorney, Agent, or Firm*—Paul A. Coletti

[57] ABSTRACT

A lancet ejector device for use in combination with a lancet injecting mechanism. The lancet ejector of the present invention enables the user to eject a lancet from the lancet injecting device without touching a used lancet.

9 Claims, 3 Drawing Sheets

LANCET EJECTOR MECHANISM

Field of the Invention

The present invention relates generally to a mechanism to pierce the skin. More specifically, the present invention relates to a mechanism whereby a needle used to pierce the skin is removed from the mechanism without human contact. Most specifically, the present invention relates to an internal mechanism in a skin Piercing device used to pierce the finger or other part of the body for glucose measurement tests; the present invention allows removal of the needle from the device without human contact.

Background of the Invention

In general, lancets have a handle and a needle extending from one end. A lancet is capable of being grasped between the thumb and index finger and made to pierce the skin, for example, the skin of a patient's finger. The lancet is removed from the incision and blood from the finger transferred to a blood collection device, such as a test tube or glucose measuring device.

In addition, of course, lancets are adaptable for use in spring loaded mechanisms. Such spring actuated lancet mechanisms are able to swiftly and without pain pierce the skin so that blood can be removed for testing. These devices have overcome much of the anxiety of the patient, especially where the incision is self-made, for example, when a diabetic makes blood glucose tests at home.

Although these lancet injector devices have become relatively economical, simple and effective in use, they still present a very troublesome problem. That is, the presently produced lancet devices all are incapable of being removed from the lancet injector mechanisms without human contact. That is, the present lancets must be inserted into the device, the device loaded, and then activated. Once the lancet pierces the skin, and a blood sample is taken from the finger or other body part, the lancet is ready for removal frOm the lancet injector mechanism. However, none of the presently produced lancet devices contain a mechanism whereby the lancet is removed from the device without human contact.

This presents a number of problems. First, of course, the patient may possibly be stuck by the needle while trying to remove the lancet. Second, if the patient inadvertently leaves the lancet within the lancet injector device, any other individual trying to remove the lancet may possibly inject himself. The possibility of infection is thus greatly increased.

Summary of the Invention

It is therefore an object of the present invention to provide an improved lancet injector mechanism which is economical, simple and effective in use and which overcomes the problem of human removal from the injector mechanism device.

It is further an object of the present invention to provide a simplified lancet ejector mechanism which can be incorporated into presently produced injector devices.

These and other objects of the present invention are accomplished in the present ejector mechanism which comprises a shifting cylindrical mechanism placed within a lancet injector device. This cylinder may be grasped by the user so that it remains stationary while the lancet injector mechanism is being cocked. While the lancet ejector remains stationary, a lancet holding mechanism moves relative to the lancet ejector mechanism. The lancet ejector mechanism pushes the lancet out of the lancet holder, and the lancet falls out of the lancet injector mechanism.

These and other aspects and advantages of the present invention will become more apparent from the following detailed description and accompanying drawings, in which:

Detailed Description of the Invention

Figure 1:
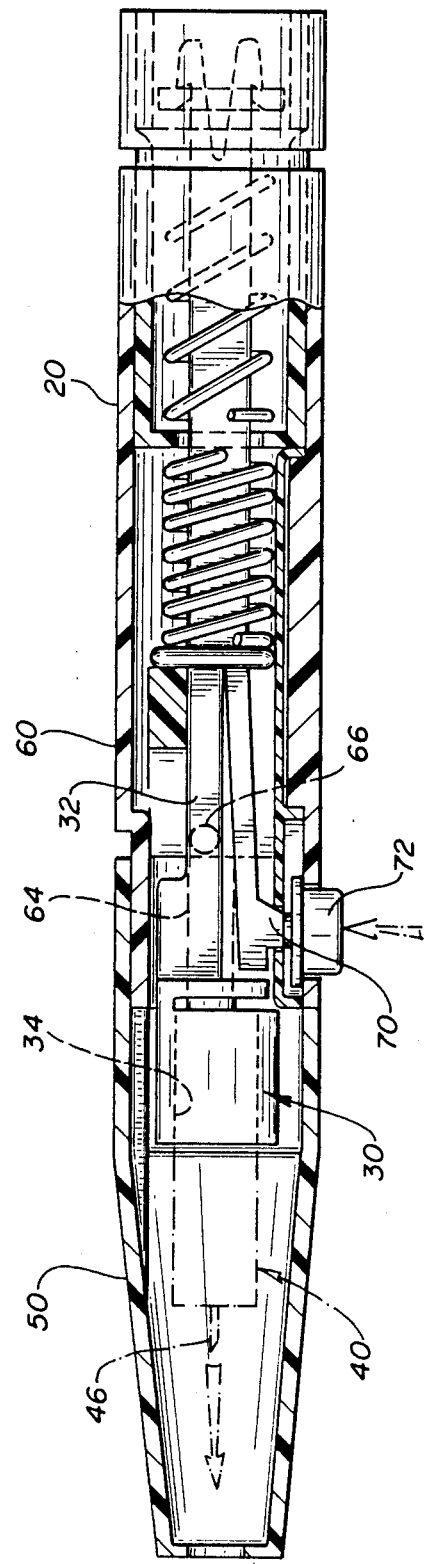
FIG. 1 is a side plan view of lancet injector device which incorporates the lancet ejector of the present invention.
Figure 2:
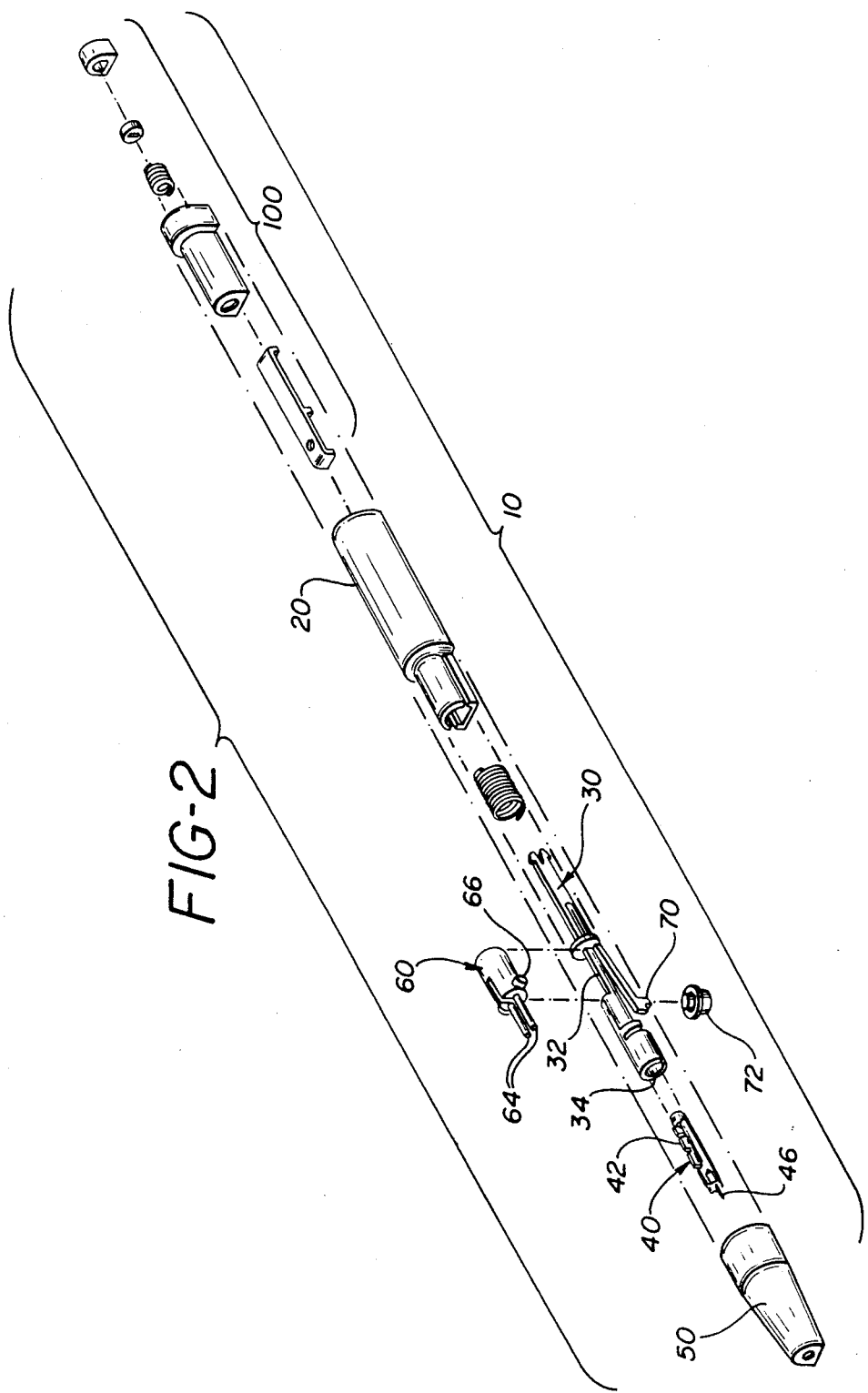
FIG. 2 is an exploded perspective view of FIG. 1.

As seen in FIGS. 1 and 2, the lancet injecting device or mechanism 10 of the present invention is comprised of a cocking mechanism 100 enclosed within a tubular channel 20. Also within tubular channel 20 there is a collar-shaped lancet holding mechanism 30, having open cylindrical ends, one end into which the lancet 40 is Placed in an interference fit. A cap 50 is emplaceable over the lancet 40 in order to create pressure on the skin of the patient.

Figure 6:
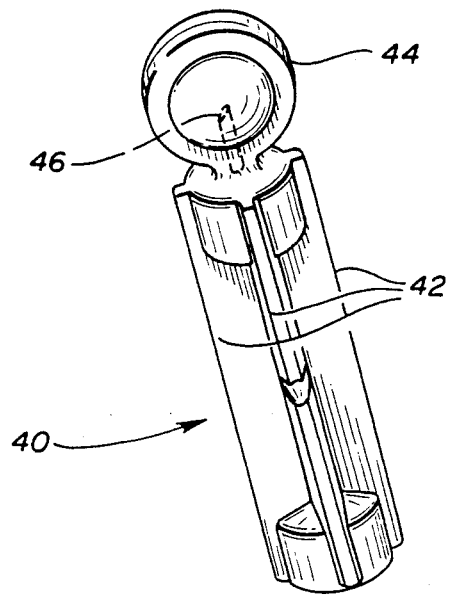
FIG. 6 is a perspective view of an unused lancet of the present invention.

As seen in FIG. 6, the lancet 40 is generally a tubular shaped member having cross shaped ridges 42, and insertable into holding mechanism 30 of the lancet injecting mechanism 10. After insertion, the lancet cap 44 is twisted off so that the lancet needle 46 becomes exposed. Thus, in operation, the lancet 40 is loaded into the lancet holder 30, and then the lancet cap 44 is twisted off to expose the needle 46. At that point, the cap 50 is placed on the tube in order to enclose the lancet needle 46.

The lancet injecting device 10 is then cocked through the use of the cocking mechanism 100, and then the lancet injecting device 10 is placed on the patient's finger. The pressure created by the cap 50 causes the finger to slightly swell, and creates a good target for the lancet needle 46. A triggering mechanism 70 held in place on tubular channel 20 is then released by pressing trigger 72. This releases the cocking mechanism 100 to activate the entire device. As the lancet injecting device 10 is fired, the lancet needle 46 pierces the skin and allows the user to draw a blood sample.

Figure 5:
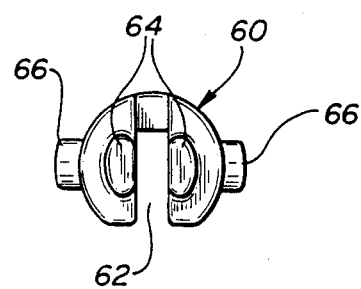
FIG. 5 is a front view of a lancet ejector of the present invention.
Figure 3:
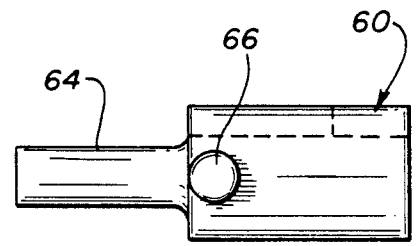
FIG. 3 is a side view of a lancet ejector of the present invention.
Figure 4:
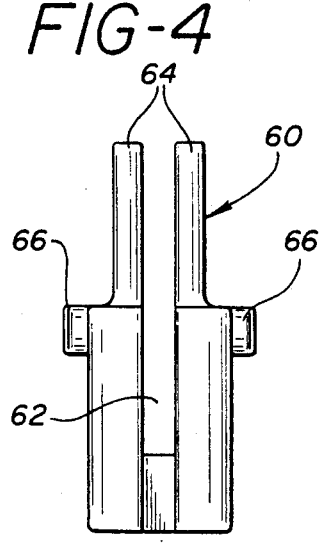
FIG. 4 is a top plan view of lancet ejector of the present invention.

It is at this point that the lancet ejector mechanism 60 of the present invention is used. The lancet ejector mechanism 60 is used in combination with the lancet holder 30, as seen in FIGS. 3, 4 and 5. The lancet ejector mechanism 60 comprises a tubular member 62 containing a slot 64 which mates with and sits on the notch 32 of lancet holder 30. The lancet ejector mechanism 60 further contains two cylindrical prongs 64 which abut the loaded lancet 40 in lancet holder 30. These prongs 64 are inserted into the tubular chamber 34 of lancet holder 30. Further, the lancet ejector 60 of the present invention contains two ears 66 which project from the lancet ejector 60.

Upon further inspection of the lancet injecting device 10, lancet holder 30 is placed within tubular channel 20 of lancet injecting device 10. Lancet ejector 60 is placed on notch 32 of the lancet holder 30. Lancet ejector 60 becomes lodged within tubular channel 20, especially since prongs 64 are placed into tubular chamber 34 of lancet holder 30. This is especially true since lancet ejector 60 seated on notch 32 faces the opposite side from which lancet ejector could come loose from tubular chamber 34. When loading the lancet 40 and cocking the lancet injecting device, lancet holder 30 moves in tandem with the lancet ejector 60. Thus, the lancet 40 is loaded within lancet holder 30, and the lancet ejector push rods 64 abut the lancet 40 throughout cocking and firing.

The lancet holder 30 in conjunction with lancet ejector 60 is then cocked in lancet injecting device 10 by cocking mechanism 100. The ears 66 projecting from the lancet ejector 60 do not touch the inside diameter of tubular channel 20.

After firing of the lancet 40, the lancet ejector 60 of the present invention is ready for use. The user removes cap 50, so that lancet needle 46 is exposed from lancet ejecting device 10. While simultaneously pressing the two ears 66 of lancet ejector 60, the user also re-cocks the mechanism. The pressure created by the user causes the ears 66 projecting from lancet ejector 60 to remain in place.

During cocking, the lancet holder 30 now moves relative to the lancet ejector 60. The slip fit of the lancet ejector channel 62 on the lancet holder notch 32 is overcome by the cocking force and the pressure on ears 66. As the lancet holder 30 retracts into the lancet injecting device 10 during cocking, the lancet ejector 60 remains stationary. Cylindrical prongs 64 of the lancet ejector 60 create a force on the lancet 40. Lancet 40 is ejected from the lancet holder 30 without being touched directly by the user. The prongs 64 cause lancet 40 to move outwardly relative to the lancet holder 30, and away from the lancet injector mechanism.

Thus, because the ears 66 of lancet ejecting device 60 transfer pressure on lancet ejector 60, the lancet ejector 60 remains stationary and reacts with the lancet 40. Lancet 40 moves relative to the lancet holder 30 during cocking of the lancet injector mechanism 10; lancet 40 falls out of the device. In this manner, lancet 40 is untouched after use.

The present invention is further understood and described in the appended claims and their equivalents.

What is claimed is:

1. A device comprising:
   a needle capable of being cocked and then injected into the skin by a spring-loaded mechanism, said needle removably inserted into said spring-loaded mechanism; and
   needle ejecting means placed on said spring-loaded mechanism and engageable with said needle such that said needle ejecting means are capable of moving relative to said spring loaded mechanism to exert a force against said needle to eject said needle from said mechanism, said needle ejecting means further comprising a pair of prongs which abut said needle.

2. A device comprising:
   lancet holding means;
   a lancet inserted into said holding means; and
   lancet ejector means attached to said holding means and movable relative to said holding means to exert a force on said lancet to eject said lancet from said holding means, said lancet ejector means comprising a pair of prongs which abut said lancet.

3. The device of claim 2 wherein said lancet holding means contains an elongated tab and said lancet ejector means contains a notch into which said tab is placed, said tab movable relative to said notch.

4. The device of claim 2 further including cocking means attached to said holding means and ear means on said lancet ejector means, onto which pressure is placed to cause said lancet ejector notch to have the capability to remain stationary during cocking of said device, said lancet ejector prongs movable relative to said lancet holder during said cocking in order to exert force on said lancet to eject said lancet from said holding means.

5. A device comprising:
   a generally cylindrical shell;
   spring loaded cocking means for cocking and firing said device and retractable within said shell;
   lancet holding means attached to said cocking means;
   a lancet attached to said holding means; and
   lancet ejector means attached to said holding means and capable of ejecting said lancet from said holding means and out of said shell; wherein said ejector means contains a pair of prongs which abut said lancet.

6. The device of claim 5 wherein said lancet ejector means moves relative to said lancet holding means to exert a force on said lancet at said prongs such that said lancet is released from said holding means.

7. The device of claim 6 wherein said holding means comprises a collar with two ends, one said end which fits about said lancet such that said lancet is held within said end, and the other said end holding said ejector means.

8. A device of claim 6 wherein said lancet holding means contains an elongated tab and said lancet ejector means contains a notch into which said tab is placed, said tab movable relative to said notch.

9. The device of claim 6 wherein said lancet ejector means contains ear means onto which pressure is placed to cause said lancet ejector notch to have the capability to remain stationary during cocking of said device, said lancet ejector prongs moveable relative to said lancet holder during said cocking in order to exert force on said lancet to eject said lancet from said holding means.

* * * * *